US00PP33852P3

(12) United States Plant Patent
Post

(10) Patent No.: US PP33,852 P3
(45) Date of Patent: Jan. 11, 2022

(54) ***CHRYSANTHEMUM* PLANT NAMED 'DLFROSC10'**

(50) Latin Name: ***Chrysanthemum* X *morifolium***
Varietal Denomination: DLFROSC10

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/089,712

(22) Filed: Nov. 4, 2020

(65) Prior Publication Data

US 2021/0136984 P1 May 6, 2021

Related U.S. Application Data

(60) Provisional application No. 62/973,983, filed on Nov. 5, 2019.

(51) Int. Cl.
*A01H 5/02* (2018.01)
*A01H 6/14* (2018.01)

(52) U.S. Cl.
USPC ..... Plt./287
CPC ..... *A01H 6/1424* (2018.05); *A01H 5/02* (2013.01)

(58) Field of Classification Search
USPC ..... Plt./287
CPC ..... A01H 5/02; A01H 5/0255
See application file for complete search history.

(56) References Cited

PUBLICATIONS http://pvpbkkt.doa.gov.my/Registration/Details.php?VarietyDenomination=DLFROSC10; May 20, 2021; 1 page.*

* cited by examiner

*Primary Examiner* — Kent L Bell
(74) *Attorney, Agent, or Firm* — C. Anne Whealy

(57) ABSTRACT

A new and distinct cultivar of *Chrysanthemum* plant named 'DLFROSC10', characterized by its upright plant habit; vigorous growth habit and rapid growth rate; dark green-colored leaves; typically disbudded and grown as a single-stem; strong upright flowering stems;
large decorative-type inflorescences with orange yellow-colored ray florets that are initially yellow green in color; relative tolerance to high production temperatures; resistance to *Fusarium* Wilt; and good postproduction longevity.

2 Drawing Sheets

Botanical designation: *Chrysanthemum* X *morifolium*.
Cultivar denomination: 'DLFROSC10'.

STATEMENT REGARDING PRIOR DISCLOSURES BY INVENTOR/APPLICANT & ASSIGNEE

An European Community Plant Breeder's Rights application for the instant plant was filed by the Assignee, Deliflor Royalties B.V. of Maasdijk, The Netherlands on Feb. 1, 2019, application number 2019/0357. Additionally, a Japanese Plant Breeder's Rights application for the instant plant was filed by the Assignee, Deliflor Royalties B.V. of Maasdijk, The Netherlands on Jul. 10, 2019, application number 34028. Foreign priority is not claimed to these applications.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFROSC10'.

The new *Chrysanthemum* plant is a product of a planned breeding program conducted by the Inventor in Maasdijk, The Netherlands. The objective of the breeding program is to create new cut flower *Chrysanthemum* plants with attractive inflorescences.

The new *Chrysanthemum* plant is a naturally-occurring whole plant mutation of *Chrysanthemum* x *morifolium* 'Delirossano', not patented. The new *Chrysanthemum* plant was discovered and selected as a single flowering plant from within a population of plants of 'Delirossano' in a controlled greenhouse environment in Maasdijk, The Netherlands in December, 2017.

Asexual reproduction of the new *Chrysanthemum* plant by vegetative terminal cuttings since December, 2017 in a controlled greenhouse environment in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFROSC10'. These characteristics in combination distinguish 'DLFROSC10' as a new and distinct *Chrysanthemum* plant:

1. Upright plant habit.
2. Vigorous growth habit and rapid growth rate.
3. Dark green-colored leaves.
4. Typically disbudded and grown as a single-stem.
5. Strong upright flowering stems.
6. Large decorative-type inflorescences with orange yellow-colored ray florets that are initially yellow green in color.
7. Relatively tolerant to high production temperatures.
8. Resistant to *Fusarium* Wilt.
9. Good postproduction longevity.

Plants of the new *Chrysanthemum* differ primarily from plants of the female parent, 'Delirossano', in ray floret color as plants of the new *Chrysanthemum* have orange yellow-colored ray florets that are initially yellow green in color whereas plants of 'Delirossano' have pale purple-colored ray florets.

Plants of the new *Chrysanthemum* can be compared to plants of *Chrysanthemum* X *morifolium* 'Delirossano Orange', not patented. In side-by-side comparisons, plants of the new *Chrysanthemum* differ primarily from plants of 'Delirossano Orange' in ray floret color as plants of the new *Chrysanthemum* have darker orange yellow-colored ray florets than plants of 'Delirossano Orange'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet comprises a side perspective view of a typical flowering stem of 'DLFROSC10' grown as a spray-type cut flower.

The photograph on the second sheet is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFROSC10'.

Parentage: Naturally-occurring whole plant mutation of *Chrysanthemum* x *morifolium* 'Delirossano', not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 74.9 cm.

*Plant height, soil level to top of inflorescence plane*.—About 78.2 cm.

*Plant (spray) diameter*.—About 22 cm.

*Flowering stem length*.—About 71.2 cm.

*Flowering stem diameter*.—About 8 mm.

*Flowering stem internode length*.—About 2.6 cm.

*Flowering stem strength*.—Strong.

*Flowering stem aspect*.—Erect.

*Flowering stem texture and luster*.—Densely pubescent; slightly glossy.

*Flowering stem color, developing*.—Close to 138B.

*Flowering stem color, developed*.—Close to 146B.

*Leaf description*.—Arrangement: Alternate; simple. Length: About 15 cm. Width: About 8.7 cm. Shape: Ovate to oblong. Apex: Abruptly acute to apiculate. Base: Attenuate. Margin: Palmately lobed, coarsely dentate; sinuses convergent and medium to deep in depth. Texture and luster, upper surface: Moderately pubescent, not rugose; moderately velvety; very slightly glossy. Texture and luster, lower surface: Moderately pubescent, prominent venation; slightly velvety; matte. Venation pattern: Pinnate, reticulate. Color: Developing leaves, upper surface: Close to between 137B and 143A. Developing leaves, lower surface: Close to 146B. Fully developed leaves, upper surface: Close to between NN137A and 147A; venation, close to 148B. Fully developed leaves, lower surface: Close to 147B; venation, close to 146C. Petioles: Length: About 2.1 cm. Diameter: About 3.5 mm by 4.5 mm. Strength: Moderately strong. Texture and luster, upper and lower surfaces: Moderately to densely pubescent; slightly glossy. Color, upper surface: Close to 148B; edges, slightly darker than 143A. Color, lower surface: Close to 146C; edges, close to 143A. Stipules: Quantity and appearance: Two leafy stipules, opposite, at the petiole attachment to the stem. Length: About 7 mm. Width: About 1 cm. Shape: Reniform. Texture and luster, upper surface: Moderately pubescent, not rugose; moderately velvety; very slightly glossy. Texture and luster, lower surface: Moderately pubescent, prominent venation; slightly velvety; matte. Color, upper surface: Close to between NN137A and 147A. Color, lower surface: Close to 147B.

Inflorescence description:

*Appearance*.—Decorative-type inflorescence form with oblanceolate-shaped ray florets and tubular disc florets; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 53 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Typically grown as a disbud-type, however, when grown as a spray-type, about 14 inflorescences develop per flowering stem.

*Inflorescence size*.—Diameter, grown as a disbud-type: About 11.5 cm. Diameter, grown as a spray-type: About 8.6 cm. Depth (height), grown as a disbud-type: About 5.9 cm. Depth (height), grown as a spray-type: About 3.4 cm. Disc diameter: About 4 mm.

*Receptacles*.—Height: About 8 mm. Diameter: About 1.6 cm. Shape: Flattened globular. Color: Close to 145B and 145D.

*Inflorescence buds*.—Height: About 1.5 cm. Diameter: About 1.3 cm. Shape: Broadly ovate to close to oblong. Texture and luster: Distally, smooth and glabrous; proximally, moderately pubescent; moderately glossy. Color: Close to 143A to 143B; immature ray florets, close to 145C tinged distally with close to N144D.

*Ray florets*.—Quantity and arrangement: About 400 arranged in about ten whorls. Length: About 4.1 cm, varying between 1.3 cm and 5.5 cm. Width: About 1.1 cm, varying between 0.3 cm and 1.5 cm. Shape: Oblanceolate; distally, strongly concave and moderately carinate. Apex: Broadly and bluntly acute. Base: Attenuate. Margin: Entire; not undulate. Aspect: Initially upright to about 45° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 164A, 164B and 166D; towards the base, close to 150C; towards the apex, close to 154A to 154B. When opening, lower surface: Close to 11B; distally, close to N144B. Fully opened, upper surface: Close to 160A; towards the base, close to 164B and 165C and at the base, close to N144B; towards the apex, close to 162A and 162B and at the apex, close to N144B; venation, similar to lamina colors; color does not change with development. Fully opened, lower surface: Close to 10D; towards the apex, close to N144B; at the base, close to 145A; venation, similar to lamina colors; color does not change with development.

*Disc florets*.—Quantity and arrangement: About 10 massed at the center of the receptacle. Length: About 1 cm. Diameter: About 1 mm. Shape: Lower 80% fused into a tube; upper 20% free. Apex: Narrowly acute. Margin, free-part: Entire. Texture and luster, inner and outer surfaces: Smooth, glabrous; glossy. Color, when opening, inner and outer surfaces: Distally, close to 150C; at the apex, close to N144C; and proximally, close to 145D. Color, fully opened, inner and outer surfaces: Distally, close to 150B; at the apex, close to N144C; proximally, close to 145D.

*Involucral bracts*.—Quantity and arrangement: About 36 arranged in about two whorls. Length: About 1.3 cm. Width: About 4 mm. Shape: Narrowly ovate. Apex: Obtuse. Base: Cuneate. Margin: Entire. Texture and luster, upper surface: Smooth, glabrous; glossy. Texture and luster, lower surface: Moderately to densely pubescent; matte. Color, upper surface: Close to 146B; midvein, close to 147A; margins, translucent and close to N155A and N199A. Color, lower surface: Close to 146B; margins, translucent and close to N155A and N199A.

*Peduncles*.—Length, terminal peduncle: About 6.5 cm. Diameter, terminal peduncle: About 6 mm. Length, third peduncle, when grown as a spray-type: About 9.3 cm. Diameter, third peduncle, when grown as a spray-type: About 3 mm. Strength: Strong. Aspect, terminal peduncle: Upright. Aspect, third peduncle, when grown as a spray-type: About 35° from the flowering stem axis. Texture and luster: Densely pubescent; very slightly glossy. Color: Close to 138B; venation, close to 137C.

*Reproductive organs*.—Androecium: Present on disc florets only. Quantity: About five per floret. Filament length: About 2 mm. Filament color: Close to 157D. Anther size: About 0.5 mm by 2 mm. Anther shape: Narrowly oblong. Anther color: Close to 8C. Pollen amount: Scarce. Pollen color: Close to 14A. Gynoecium: Present on both ray and disc florets. Quantity: One per floret. Pistil length: About 1.1 cm. Style length: About 1 cm. Style color: Close to 145A. Stigma diameter: About 1 mm. Stigma shape: Cleft, decurrent. Stigma color: Close to 154B. Ovary color: Close to 145A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum* spp. *chrysanthemi* (FoNL1)). To date, plants of the new *Chrysanthemum* have not been observed to be resistant or tolerant to pests and other pathogens common to *Chrysanthemum* plants grown under commercial conditions.

Temperature tolerance: Plants of the new *Chrysanthemum* have been observed to tolerate temperatures ranging from about −12 ° C. to 35° C. and to be suitable for USDA Hardiness Zones 8 to 10.

It is claimed:

1. A new and distinct *Chrysanthemum* plant named 'DLFROSC10' as illustrated and described.

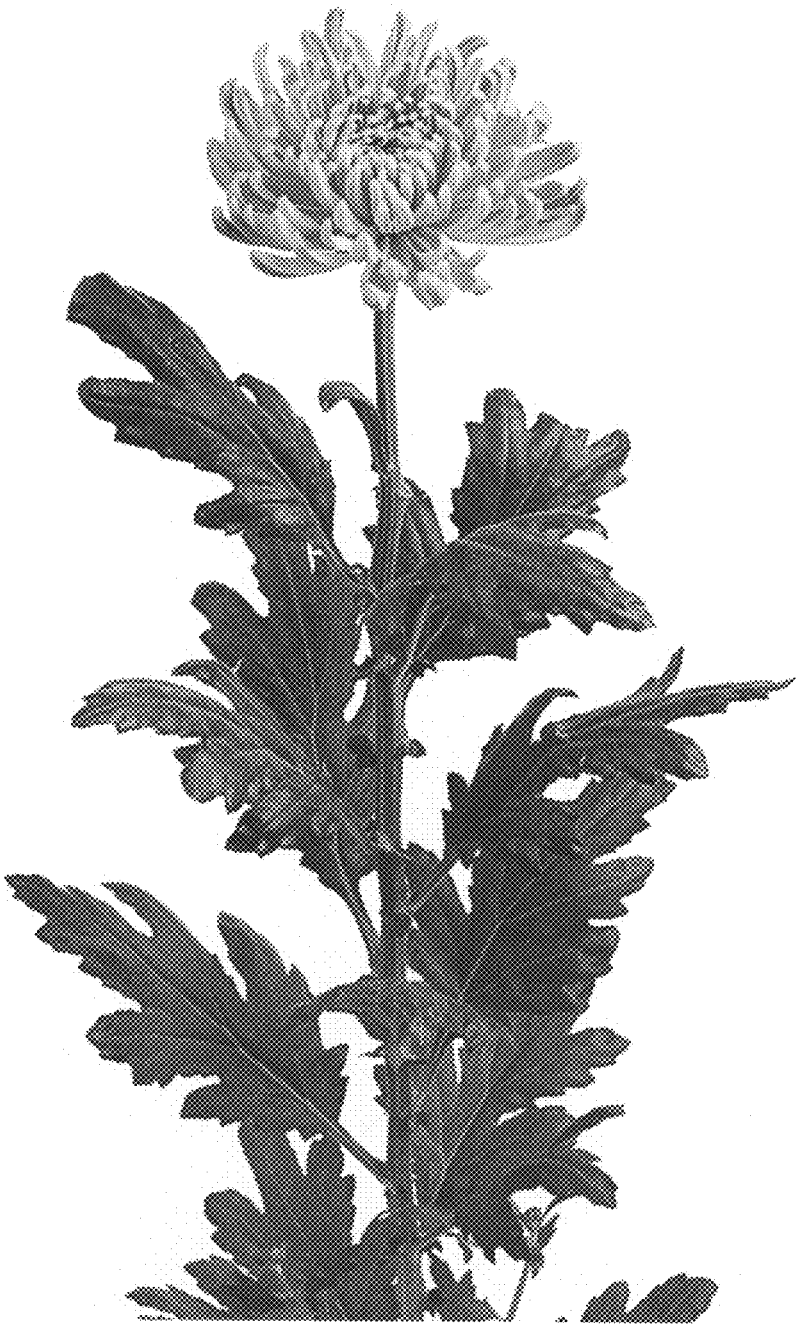

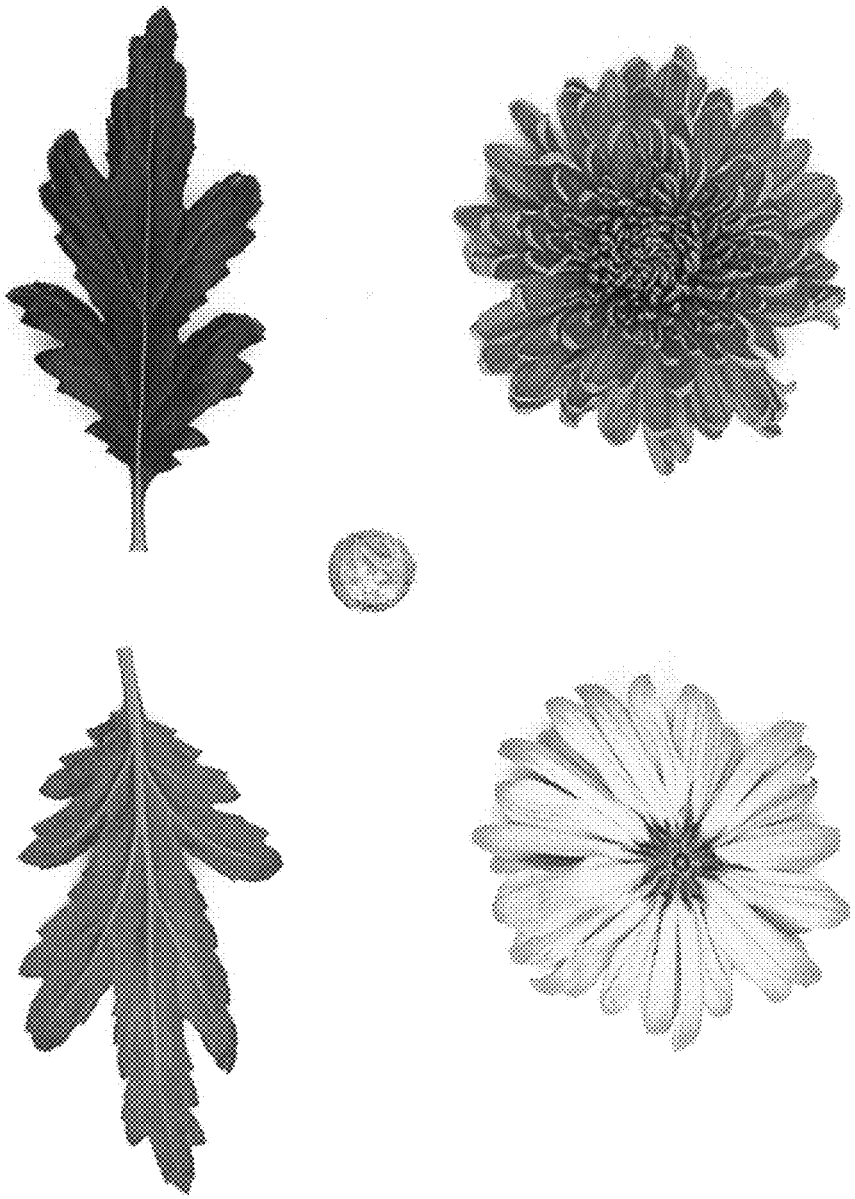

* * * * *